United States Patent [19]
O'Connor

[11] Patent Number: 5,190,055
[45] Date of Patent: Mar. 2, 1993

[54] DEVICE FOR RESTRAINING A PERSON

[76] Inventor: Wayne O'Connor, 1810 E. 109th St., Indianapolis, Ind. 46280

[21] Appl. No.: 859,040

[22] Filed: Mar. 27, 1992

[51] Int. Cl.$^5$ .......................... A61B 19/00; A61F 5/37
[52] U.S. Cl. ..................................... 128/869; 128/876
[58] Field of Search ............... 128/870, 869, 874, 875, 128/876; 5/628, 648, 650

[56] References Cited

U.S. PATENT DOCUMENTS

| | | | |
|---|---|---|---|
| 794,457 | 7/1905 | Gaiter | 128/876 |
| 919,159 | 4/1909 | Goddard | 5/628 |
| 2,215,454 | 9/1940 | Condit | 128/870 |
| 2,361,789 | 10/1944 | Nicholas | 5/628 |
| 2,788,530 | 4/1957 | Ferguson | 5/628 |
| 2,947,007 | 8/1960 | Oades | 5/628 |
| 3,158,875 | 12/1964 | Fletcher | 5/628 |
| 3,358,141 | 12/1967 | Hoffmann | 128/870 |
| 3,526,222 | 9/1970 | Dreibelbis | 128/870 |
| 3,933,154 | 1/1976 | Cabansag | 128/870 |
| 4,515,155 | 5/1985 | Wagemann | 128/876 |
| 4,679,260 | 7/1987 | Frettem | 5/628 |
| 4,970,739 | 11/1990 | Bradford | 128/870 |

FOREIGN PATENT DOCUMENTS

0028613 of 1912 United Kingdom ................ 128/870

Primary Examiner—Robert A. Hafer
Assistant Examiner—Michael Brown
Attorney, Agent, or Firm—Woodard, Emhardt, Naughton, Moriarty & McNett

[57] ABSTRACT

A soft restraint device for restraining a person to a frame, such as a bed frame, is disclosed including a waist strap, a pair of thigh straps, a pair of knee straps, and a pair of ankle straps. The restraining straps are innerconnected by left side and right side longitudinal straps running along the outside of the person's legs and left side and right side longitudinal straps running along the inside of the person's legs. Stirrup members are provided under the feet. Inter-leg straps are further provided preventing abduction of the person's legs. Restraining straps, such as tethers, are provided to secure the strap structures to a bed frame.

17 Claims, 3 Drawing Sheets

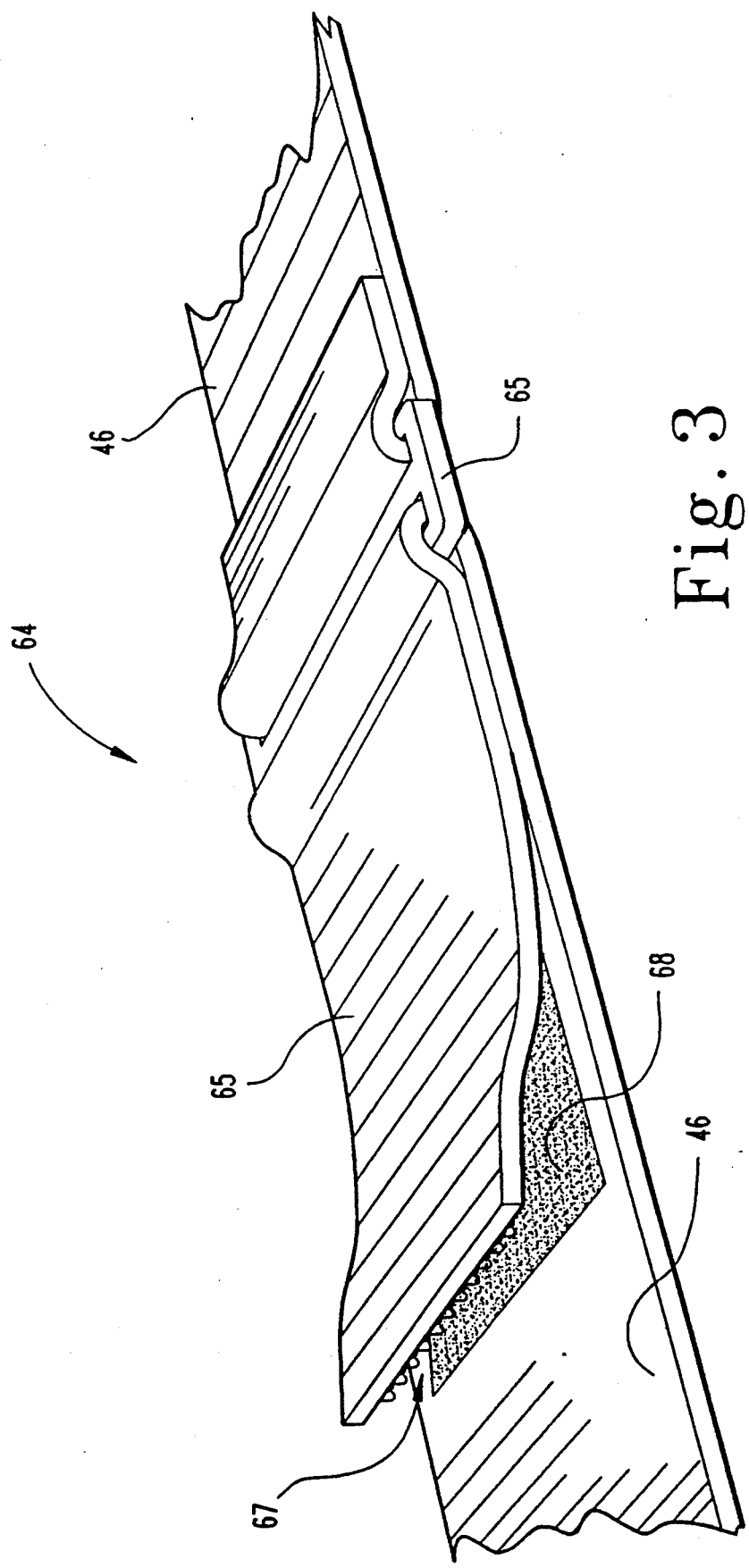

DEVICE FOR RESTRAINING A PERSON

BACKGROUND OF THE INVENTION

The present invention relates generally to a device for restraining a person to a frame, such as a bed frame or the like, and more specifically relates to a soft restraint device having straps around the person's leg for restraint.

There is a need to provide restraints, particularly for medical patients needing to be restrained to a bed to prevent injury to themselves and to others. Although various devices have been developed, they have various shortcomings. Typically, it is not uncommon for restraints to comprise a loop around the ankle of the person which is secured to the bed frame. While providing some restraint, such devices are not entirely satisfactory, especially for a very active or violent patient. However, it is desirable to have a device which, while providing adequate restraint, also is reasonably easy and comfortable to use without requiring undue time or effort.

Various restraining devices are disclosed in U.S. Pat. No. 4,911,105 to Hocum, U.S. Pat. No. 826,648 to Challenger, U.S. Pat. No. 794,457 to Gaiter, U.S. Pat. No. 845,523 to Cass, U.S. Pat. No. 2,295,806 to Peterson, and U.S. Pat. No. 4,841,961 to Burlage et. al. Other patents which may be of interest are U.S. Pat. Nos. 4,256,098 to Swan et. al., U.S. Pat. Nos. 3,502,073 to Stanley, 4,657,003 to Wirtz, 976,564 to Goodson, and 5,027,833 to Calkin. However, none of these devices provide the features and advantages which are provided by the present invention described more fully below.

SUMMARY OF THE INVENTION

The present invention provides a device for restraining a person to a frame, such as a bed frame or the like including a set of at least four leg straps disposable around the left and right upper and lower legs of the person. A left side longitudinal strap and a right side longitudinal strap are provided, each running along the length of the person's leg, wherein the longitudinal leg straps are secured to the respective leg straps. A plurality of means for securing the leg straps to the bed frame are provided, such as tethers. Optionally, a waist strap may be provided which is connected to the upper leg straps, preventing the upper leg straps from riding downwardly off the person's upper legs.

The present invention further provides a device for restraining a person comprising a set of leg straps disposable around the left and right lower leg portions of the person and a pair of longitudinal straps running along the length of the person's legs which are secured to the respective lower leg straps. A waist strap is further provided and connected to the lower leg straps, and a second pair of longitudinal straps disposable along the length of the inside of the person's legs. Left and right stirrup members are provided along the bottom of the person's feet to prevent the leg straps from riding upwardly towards the person's crotch. A plurality of means for securing the leg straps to the bed frame is provided.

One object of the present invention is to provide an improved device for restraining a person.

Another object of the present invention is to provide a device which effectively restrains a person's lower body, and in particular the stronger parts of the lower body including the thighs and the knees.

Another object of the present invention is to restrain the legs of a person against adduction and abduction.

Another object of the present invention is to provide leg restraints which are prevented from riding upwardly or downwardly off of the person's leg portions to be restrained.

These and other objects and improvements will be apparent from the written description and drawing figures herein.

DESCRIPTION OF THE DRAWINGS

FIG. 3 is a perspective detail of a strap coupling of the present invention shown in isolation.

DESCRIPTION OF THE PREFERRED EMBODIMENT

Figure 1:
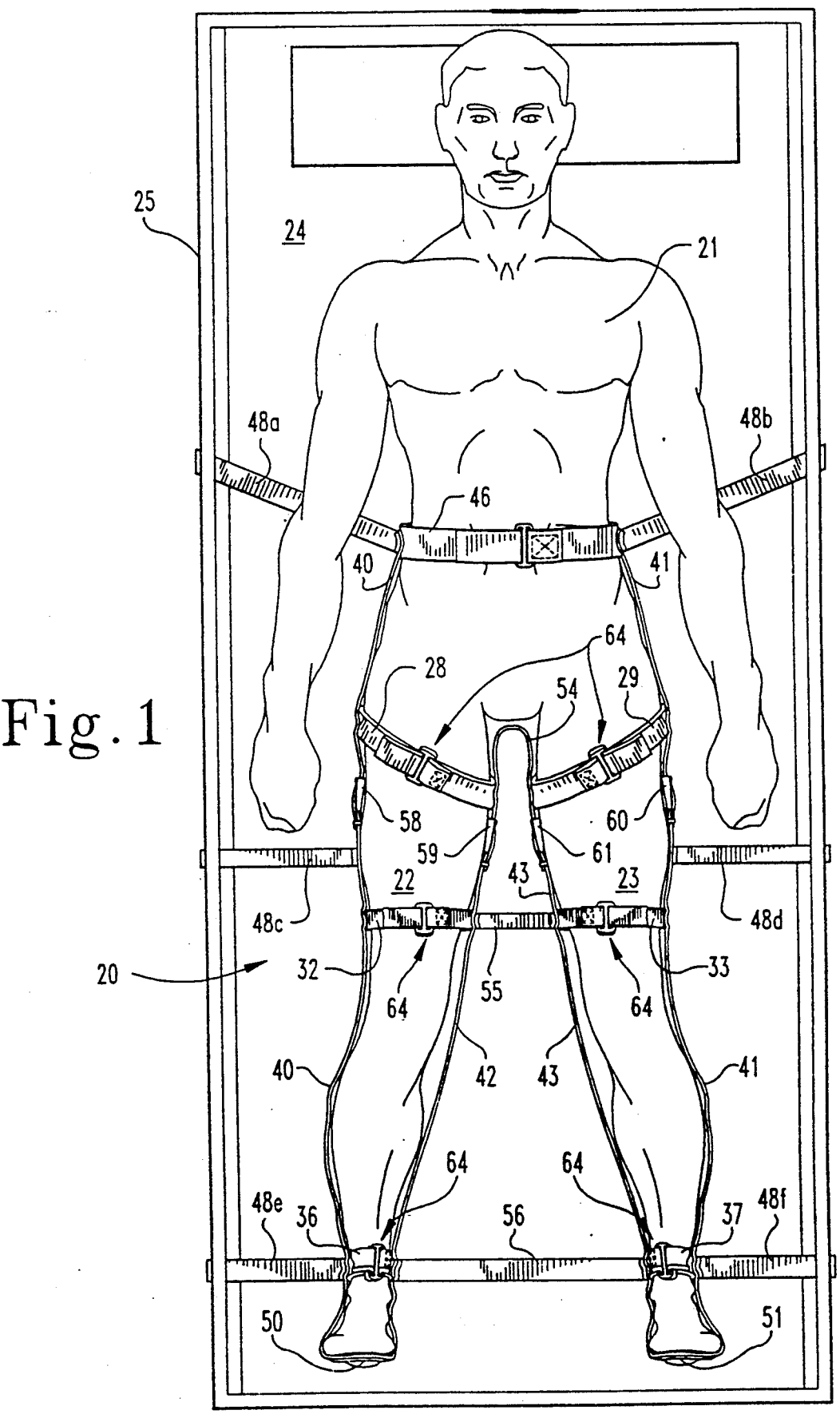
FIG. 1 is a top plan view of one embodiment of the present invention restraining a person on top of a bed.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated devices and processes, and such further applications of the principles of the invention as illustrated therein being contemplated as would normally occur to one skilled in the art to which the invention relates.

Figure 2:
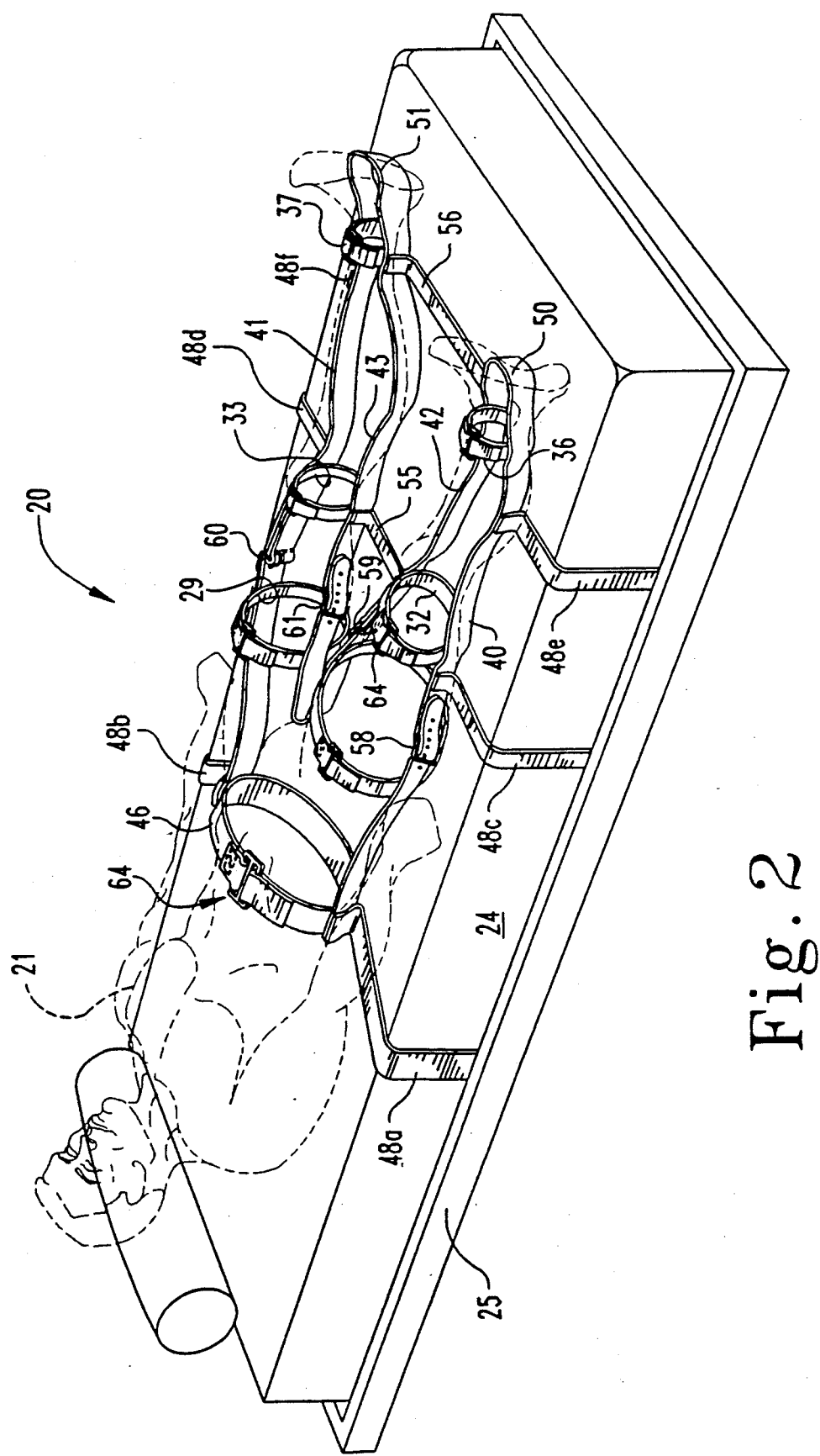
FIG. 2 is a perspective view of the device of FIG. 1 with the restrained person shown in phantom lines.

Referring to FIGS. 1 and 2, a soft restraint device 20 for restraining a person 21 on top of bed 24 and to bed frame 25 is illustrated. The person has a right leg 22 and a left leg 23 as well as the other normal human anatomical parts illustrated. The device is particularly well suited for restraining a person on their back on top of a bed, but also may have application to restraining the person to other frame structures, such as chairs and the like when appropriate.

Restraining device 20 is preferably symmetric in construction and includes a right upper leg strap 28 and a left upper leg strap 29 which, as illustrated, are thigh straps around the thighs of the person. The device further includes right intermediate strap 32 and left intermediate strap 33 around the legs which are on or near the knees of the person. Furthermore, right lower leg strap 36 and left lower leg strap 37 are provided, preferably as ankle straps around the ankles of the person. Each of these three pairs of leg straps are secured to longitudinal straps, such as right outer longitudinal strap 40, left outer longitudinal strap 41, right inner longitudinal strap 42 and left inner longitudinal strap 43. In the preferred embodiment, straps 42 and 43 are disposed along the inside of the person's legs inbetween legs 22 and 23, and straps 40 and 41 are disposable along the outside of the person's leg opposite straps 42 and 43. In the preferred embodiment, these four longitudinal straps are constructed from a singular piece of strap material starting at waist strap 46 on the right side, running downwardly towards the feet as strap 40, around the bottom of the right foot as right stirrup 50, running upwardly towards the crotch as strap 42, traversing the crotch region as inter-leg strap 54, running downwardly towards the left foot as strap 43, running along the bottom of the left foot as left stirrup 51, and running upwardly towards waist strap 46 along the left outside edge of the patient as strap 41. The set of leg straps 28, 29, 32, 33, 36 and 37 are secured to these longitudinal straps, such as by stitching, adhesive, rivoting, intergral formation, or otherwise. Waist strap 46 is likewise secured to straps 40 and 41 and is disposable around the waist of the person being restrained. This entire structure is secured to the bed and bed frame by any variety of structures, which in the preferred embodiment, as shown as tethers 48a–48f. The six illustrated tethers are securely attached to the strap system previously described and restrain the patient to the bed. Furthermore, particularly with respect to tethers 48c, 48d, 48e and 48f, the tethers prevent adduction of the person's legs inwardly towards each other. Typically the tethers are tied with knots to frame 25, although other securement (buckles, locks, etc.) may be used.

Inter-leg strap 55 and inter-leg strap 56 are both secured to straps 42 and 43 to prevent abduction of the legs. In this way, a violent person will be restrained from abduction, such as kicking his legs outwardly towards an attendant or other person along side the bed. All of the straps and tethers in the preferred embodiment are made of flexible material, such as natural or synthetic material. Although the "straps" are preferably flat, other configurations such as round cord are included within the meaning of this term.

Each of the six leg straps as well as the waist strap 46 preferably include a mechanism for selectively securing and unsecruing the strap around the body part of the person to be restrained. In the preferred embodiment, a representative example is illustrated in FIG. 3 as strap coupling 64. This particular structure includes a loop body or buckle structure 65 which has a stitched loop on one side thereof and on the other side has a folded back portion 66 having hook material 67 on the inside thereof. Corresponding nap material 68 is provided along strap 46 to engage the hook material 67. Such hook and nap structure may be made from the Velcro ™ brand fastener. Other optional structures such as conventional buckles, snaps, knots or otherwise may be used. As stated, the strap couplings preferably are also present on each of the leg straps. In this way, the restraining system may be pre-secured to the bed frame 25, such as by tying it down with knots or otherwise and with the strap couplings, such as coupling 64, in an uncoupled mode. The person to be restrained is laid down on top of the device and the six leg straps and the waist strap are then disposed around the appropriate body parts and fastened securely closed. Naturally, it is preferably that if such a system is used the person's hands and arms are likewise restrained, particularly to prevent them from unsecuring the strap couplings. The present invention may optionally incorporated with further structure to restrain the upper body portion of the patient, including the arms. However, in the preferred embodiment it is contemplated that the present invention does not include such upper body restraint, with such function being accomplished with separate restraints.

Buckles or similar adjustment mechanisms 58, 59, 60 and 61 optionally may be provided along straps 40, 42, 41 and 43 respectively, as illustrated, to allow the length of device 20 to be selectively adjusted. In this way, the stirrups 50 and 51 may effectively be moved closer or further from the waist strap to accomodate a taller or a shorter person. However, these features may be omitted with various sizes of the present invention being made available to accomodate different size persons.

The present invention is particularly advantageous in that waist strap 46 and its accompanying tethers prevent, by virtue of straps 40 and 41, the thigh straps 28 and 29 and the knee straps 32 and 33 from riding downwardly towards the person's feet and off of the upper leg (thigh and knee). Conversely, the stirrups 50 and 51 along with the longitudinal straps advantageously prevent the leg straps from riding upwardly, and in particular prevent straps 28 and 29 from riding upwardly into the crotch of the person, causing discomfort. Each of the straps described above are preferably flexible adding to the comfort of the person restrained. Accordingly, the present invention provides safe and comprehensive lower-body patient restraint and provides safety while also providing relatively convenient attachment of the device to the person and also providing a relative lack of shifting of the device with respect to parts of the person's legs.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A soft restraint device for restraining a person to a frame, such as a bed frame or the like, comprising:
   a set of at least four leg straps, comprising
   (a) a left upper leg strap disposable around a left upper leg of the person;
   (b) a right upper leg strap disposable around a right upper leg of the person;
   (c) a left lower leg strap disposable around a left lower leg portion below a left knee of the person; and,
   (d) a right lower leg strap disposable around a right lower leg portion below a right knee of the person;
   a first left side longitudinal flexible strap running along the length of the person's left leg, wherein said first left side longitudinal strap is secured to said left upper leg strap and to said left lower leg strap;
   a second left side longitudinal flexible strap disposable along an elongated length of the inside of the person's left leg, wherein said second left side longitudinal strap is secured to said left side upper leg strap and to said left lower leg strap, wherein said first left side longitudinal strap is disposable along the outside of the person's left leg;
   a first right side longitudinal flexible strap running along the length of the person's right leg, wherein said first right side longitudinal strap is secured to said right upper leg strap and to said right lower leg strap;
   a second right side longitudinal flexible strap disposable along an elongated length of the inside of the person's right leg, wherein said second right side longitudinal strap is secured to said right side upper leg strap and to said right lower leg strap, wherein said first right side longitudinal strap is disposable along the outside of the person's right leg, wherein said left and right longitudinal straps are interconnected to form a unitary restraint device; and, a plurality of means for securing said set of leg straps to the bed frame.

2. The device of claim 1 and further comprising:
a waist strap disposable around a waist of the person; and,
means connecting said waist strap to said left and right upper leg straps and preventing said upper leg straps from riding downwardly off of the person's upper legs.

3. The device of claim 2 and further comprising at least one inter-leg strap located between the person's legs and securing left side and right side pairs of said set of leg straps to prevent abduction of the person's legs.

4. The device of claim 3 and further comprising:
a left intermediate strap disposable around the person's left leg on or near the left knee, wherein said left intermediate strap is located along the left leg inbetween said left upper leg strap and said left lower leg strap, and wherein said left intermediate strap is secured to said first left side longitudinal strap; and,
a right intermediate strap disposable around the person's right leg on or near the right knee, wherein said right intermediate strap is located along the right leg inbetween said right upper leg strap and said right lower leg strap, and wherein said right intermediate strap is secured to said first right side longitudinal strap.

5. The device of claim 4 and further comprising:
a left stirrup member along a bottom of the person's left foot; and
a right stirrup member along a bottom of the person's right foot, wherein said right and left stirrup members prevent said set of leg straps from riding upwardly toward the person's crotch.

6. The device of claim 5 wherein said inter-leg strap is located between and secures said left and right intermediate straps together, and further comprising a second inter-leg strap located between and securing said left and right lower leg straps together.

7. The device of claim 6 wherein said plurality of means for securing said set of leg straps to the bed comprise at least four tethers.

8. The device of claim 3 and further comprising:
a left intermediate strap disposable around the person's left leg on or near the left knee, wherein said left intermediate strap is located along the left leg inbetween said left upper leg strap and said left lower leg strap, and wherein said left intermediate strap is secured to said first left side longitudinal strap; and,
a right intermediate strap disposable around the person's right leg on or near the right knee, wherein said right intermediate strap is located along the right leg inbetween said right upper leg strap and said right lower leg strap, and wherein said right intermediate strap is secured to said first right side longitudinal strap.

9. The device of claim 2 and further comrprising:
a left intermediate strap disposable around the person's left leg on or near the left knee, wherein said left intermediate strap is located along the left leg inbetween said left upper leg strap and said left lower leg strap, and wherein said left intermediate strap is secured to said first left side longitudinal strap; and a right intermediate strap disposable around the person's right leg on or near the right knee, wherein said right intermediate strap is located along the right leg inbetween said right upper leg strap and said right lower leg strap, and wherein said right intermediate strap is secured to said first right side longitudinal strap.

10. The device of claim 2 and further comprising:
a left stirrup member along a bottom of the person's left foot; and
a right stirrup member along a bottom of the person's right foot, wherein said right and left stirrup members prevent said set of leg straps from riding upwardly toward the person's crotch.

11. The device of claim 1 and further comprising at least one inter-leg strap located between the person's legs and securing left side and right side pairs of said set of leg straps to prevent abduction of the person's legs.

12. The device of claim 11 wherein said inter-leg strap is located between and secures said left and right intermediate straps together, and further comprising a second inter-leg strap located between and securing said left and right lower leg straps together.

13. The device of claim 1 and further comprising:
a left stirrup member along a bottom of the person's left foot; and
a right stirrup member along a bottom of the person's right foot, wherein said right and left stirrup members prevent said set of leg straps from riding upwardly toward the person's crotch.

14. The device of claim 1 and further comprising:
a left intermediate strap disposable around the person's left leg on or near the left knee, wherein said left intermediate strap is located along the left leg inbetween said left upper leg strap and said left lower leg strap, and wherein said left intermediate strap is secured to said first left side longitudinal strap; and,
a right intermediate strap disposable around the person's right leg on or near the right knee, wherein said right intermediate strap is located along the right leg inbetween said right upper leg strap and said right lower leg strap, and wherein said right intermediate strap is secured to said first right side longitudinal strap.

15. The device of claim 1 and further comprising:
means for adjusting length of said left side longitudinal strap to allow selective lengthening and shortening of said left side longitudinal strap to fit various sized persons; and,
means for adjusting length of said right side longitudinal strap to allow selective lengthening and shortening of said right side longitudinal strap to fit various sized persons.

16. A soft restraint device for restraining a person to a frame, such as a bed frame or the like, comprising:
a set of at least two leg straps, comprising
(a) a left lower leg strap disposable around a left lower leg portion below a left knee of the person; and,
(b) a right lower leg strap disposable around a right lower leg portion below a right knee of the person;
a first left side longitudinal strap running along the length of the person's left leg, wherein said first left side longitudinal strap is secured to said left lower leg strap;

a first right side longitudinal strap running along the length of the person's right leg, wherein said first right side longitudinal strap is secured to said right lower leg strap; and, a waist strap disposable around a waist of the person;

means connecting said waist strap to said left and right lower leg straps and preventing said lower leg straps from riding downwardly;

a second left side longitudinal strap disposable along an elongated length of the inside of the person's left leg, wherein said second left side longitudinal strap is secured to said left lower leg strap, wherein said first left side longitudinal strap is disposable along the outside of the person's left leg;

a second right side longitudinal strap disposable along an elongated length of the inside of the person's right leg, wherein said second right side longitudinal strap is secured to said right lower leg strap, wherein said first right side longitudinal strap is disposable along the outside of the person's right leg;

a left stirrup member along a bottom of the person's left foot; and a right stirrup member along a bottom of the person's right foot, wherein said right and left stirrup members prevent said set of leg straps from riding upwardly toward the person's crotch; and, a plurality of means for securing said set of leg straps to the bed frame.

17. The device of claim 16 and further comprising at least one inter-leg strap located between the person's legs and securing left side and right side pairs of said set of leg straps to prevent abduction of the person's legs.

* * * * *